United States Patent [19]
Turchin et al.

[11] Patent Number: 5,889,201
[45] Date of Patent: Mar. 30, 1999

[54] CHARACTERIZATION OF FLUID MISTING

[75] Inventors: Henry Turchin, Loveland; Edward Harry Rolfert, Cincinnati, both of Ohio

[73] Assignee: Cincinnati Milacron Inc., Cincinnati, Ohio

[21] Appl. No.: 962,549

[22] Filed: Oct. 31, 1997

[51] Int. Cl.$^6$ .............. B05B 1/28; A61M 11/02; B01D 37/04; G01N 7/00
[52] U.S. Cl. .............. 73/53.01; 73/61.43; 239/338; 261/78.1; 261/DIG. 65
[58] Field of Search .............. 73/53.01, 19.1, 73/61.43; 137/896; 239/338, 370; 261/78.1, DIG. 65

[56] References Cited

U.S. PATENT DOCUMENTS

| | | | |
|---|---|---|---|
| 3,643,624 | 2/1972 | Eng et al. .............. | 116/137 A |
| 4,116,387 | 9/1978 | Kremer et al. .............. | 239/338 |
| 4,456,179 | 6/1984 | Kremer .............. | 239/338 |
| 4,670,137 | 6/1987 | Koseki et al. .............. | 210/96.1 |
| 5,259,813 | 11/1993 | Abthoff et al. .............. | 454/75 |
| 5,346,132 | 9/1994 | Hahn .............. | 839/71 |
| 5,463,951 | 11/1995 | Waizmann et al. .............. | 101/423 |
| 5,524,729 | 6/1996 | Boelkins .............. | 184/55.1 |
| 5,597,044 | 1/1997 | Roberts et al. .............. | 169/46 |
| 5,646,336 | 7/1997 | Thompson et al. .............. | 73/61.43 |

OTHER PUBLICATIONS

N. DeMarco; NIOSH Urges Lower Fluid Mist Exposures, Lubes 'N' Greases; May, 1996, pp. 40–43.

T.L. Chan, J.B D'Arcy, J. Siak; Size Characteristics of Machining Fluid Aerosois in an Industrial Metal Working Environment, Applied Occupational and Environmental Hygiene; Mar., 1990, pp. 162–170.

R.S. Marano, J.M. Smolinksi, R.L. Messick, C.W. Manke, Jr., E. Gulari; Polymer Additives as Mist Suppressants in Metal Cutting Fluids, presented 23 Jul. 1996 at GM Technical Center, Detroit, MI.

Primary Examiner—Hezron Williams
Assistant Examiner—J. David Wiggins
Attorney, Agent, or Firm—John W. Gregg

[57] ABSTRACT

A method and apparatus for measuring a misting property of fluids, the method and apparatus simulating mist generation of fluids in machining processes. Fluid is supplied to mist generating means in an enclosure and energy input to the fluid by the mist generating means is controlled. Mist laden gas flows from the vicinity of mist generation to a mist concentration measuring means. Droplets of relatively large mass are removed from the mist prior to the flow of gas reaching the mist concentration measuring means. To further simulate machining processes, the fluid of interest is recirculated from a reservoir through the mist generating means. Mist concentration measurements produced under the same conditions for fluids of different compositions are compared to characterize the misting properties of fluids.

18 Claims, 1 Drawing Sheet

CHARACTERIZATION OF FLUID MISTING

BACKGROUND OF THE INVENTION

I. Field of the Invention

This invention relates to characterization of misting properties of fluids. In particular, this invention relates to methods and apparatus for measuring a misting property of metalworking fluids.

II. Description of Related Art

Many industrial processes make use of fluids for lubricating and cooling, particularly machining processes, i.e. processes involving mechanical cutting or forming of workpieces. Machining processes include cutting processes such as sawing, drilling, milling, grinding, turning, broaching, reaming, tapping, and planing, and forming processes such as bending, ironing, punching, rolling, stamping, die cutting, and forging. When lubricating and cooling fluids are applied as streams to the interface between the workpiece and tool, mists can be generated as a function of energy input to the fluids by the mechanics of the machining process. Such generation of mists is most common in processes in which the fluid stream contacts the periphery of a rotating member, whether a tool, as in drilling, milling, tapping, reaming, or boring, or a workpiece as in turning or some types of grinding. In such processes, sufficient shear stresses are developed by contact of the fluid with the rotating member to cause separation of droplets from the fluid stream, and to propel the droplets into the surrounding atmosphere. Such mist generation is particularly prevalent in grinding operations by virtue of the relatively high surface speeds at which grinding is performed, hence high energy input to the fluid, the relatively high volume of fluid applied, hence large quantities of fluid to be converted to droplets, and the rough surface of grinding wheels tending to capture fluids at the surface and hence increase shear stresses imparted to fluids.

The nature of mist generation in industrial processes is such that a broad spectrum of droplet masses is produced. Further, droplets are propelled from these processes in varying directions and are, consequently, subject to collisions with other droplets, altering droplet masses and energies. In general, these processes produce droplets which are subject to different transport effects. In particular, transport of droplets of relatively large mass will be dominated by inertia and gravity, while transport of droplets of relatively small mass will be dominated by Brownian motion. The droplets of smaller mass are known to contribute to the persistence of mists long after mist generation has ceased. As the transport of fluid droplets and the persistence of mists contribute to potential human exposure in industrial operations, and the concentration of mists in industrial environments is subject to regulation as relating to health and safety in the workplace. Of particular concern in this regard are droplets small enough to be respirable, these smaller droplets being susceptible of transportation farthest from the source. Regulations set limits on the concentration of mist in the workplace at locations proximate to industrial equipment where production personnel can be expected to be exposed to such mists. In addition to concerns of exposure of personnel, generation of mists from machining fluids has the attendant disadvantages of increasing loss of fluid, with potential loss of functionality as fluid composition is changed, and deposition on surfaces of facilities and equipment of contaminants carried in such mists.

In light of the adverse consequences of mist generation, and particularly in light of the regulation of mist concentration in the workplace, it is desirable to characterize the misting properties of machining fluids. In particular, it is desirable to characterize the influence on misting properties of fluid constituents to identify fluids and constituents which have the potential for reducing mist generation while maintaining desirable functions of the fluids. Hence, methods and apparatus for measuring misting properties of machining fluids in industrial processes are needed.

It is known to measure mist generation in production environments, however it is clearly impractical to dedicate use of production machinery to measurements required for characterization of misting properties of the spectrum of machining fluids to be encountered in industrial operations. Besides the obvious high cost of equipment utilization, the use of such machines increases the difficulty of controlling conditions relevant to characterization of fluid properties. Hence, methods and apparatus are needed for characterization of misting properties of aqueous fluids under controlled conditions which simulate an industrial process while permitting elimination of variables difficult to document in a production environment.

Known laboratory techniques for controlled generation of mists generally lack one or more characteristics of machining processes which influence generation of mists in industrial production. For example, it is known to use atomizers to produce mists from a reservoir of the fluid under test. Atomizers, typically single point sources, do not generally produce random motion of fluid droplets characteristic of machining processes. Further, while production equipment recirculates machining fluids through the machining process, hence recombines mist droplets collected on machine surfaces with other fluid from a reservoir, laboratory equipment known for studying mists does not provide for collection of mist, its recombination with fluid used for mist generation and recirculation of the resulting fluid.

SUMMARY OF THE INVENTION

It is an object of the present invention to provide methods and apparatus for characterization of misting properties of machining fluids used in industrial processes.

It is a further object of the present invention to provide methods and apparatus for measuring a misting property of machining fluids by simulation of mist generation in industrial processes.

Other objects and advantages of the present invention shall become apparent from the drawings and the following description.

In accordance with the aforesaid objects a method and apparatus are provided for measuring a misting property of fluids. Mist is generated in an enclosure from which a flow of mist laden gas is directed to a mist concentration measuring instrument. Droplets of relatively large mass are removed from the gas flow prior to the gas reaching the mist concentration measuring instrument, simulating removal of such droplets from mist by natural effects in industrial processes. To further simulate effects common to industrial processes, recirculation of fluid is provided between a fluid reservoir and mist generating means.

DETAILED DESCRIPTION OF THE PREFERRED EMBODIMENT

Figure 2:
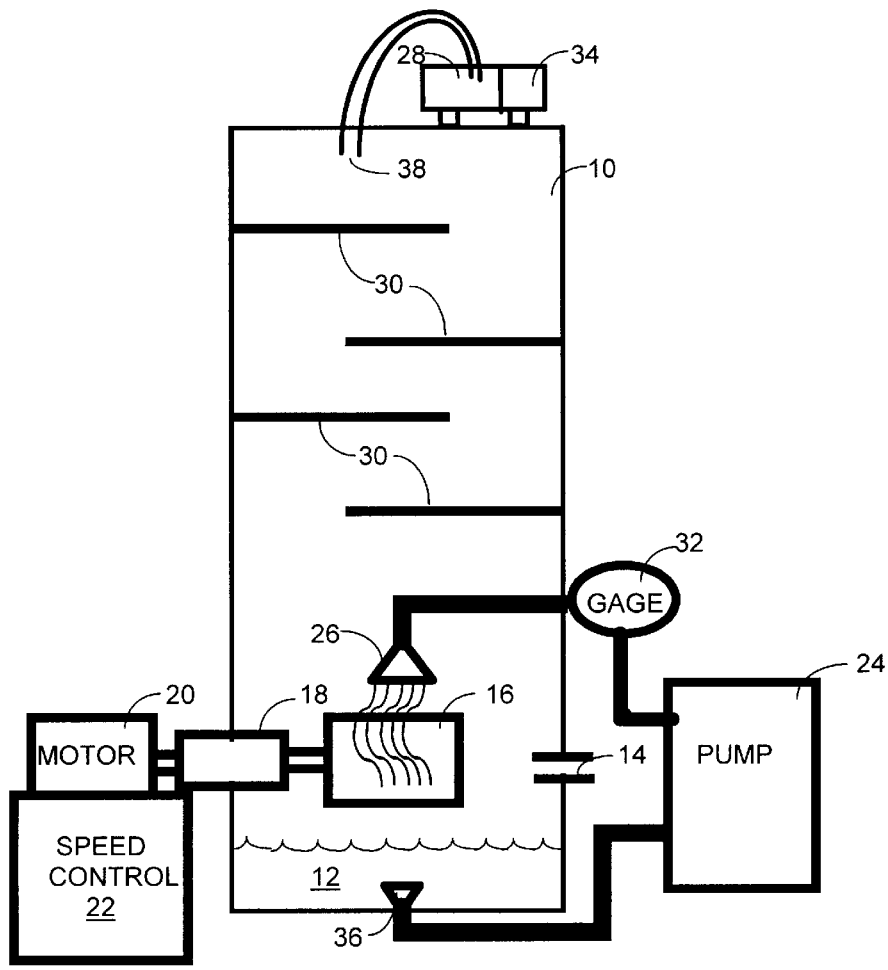
FIG. 2 is a block diagram of mist measuring apparatus in accordance with the invention.

It is common practice in the industrial fluids industry to refer to functional fluids used in machining processes as "metalworking" or "cutting" fluids or "coolants" irrespective of the nature of the process in which used and the workpiece material. Hence such fluids may be used in all manner of mechanical processing of workpieces, including without limitation, milling, drilling, tapping, reaming, grinding, polishing, forming, rolling, ironing and bending. Further, such fluids are used in processing of metallic, plastic, ceramic and composite materials. Herein, the terms "machining fluids", "metalworking fluids", "cutting fluids" and "coolants" shall be used interchangeably.

Both aqueous fluids and straight oils are used as machining fluids in industrial processes. Straight oils are compositions of petroleum oils and additives, such as antioxidants, extreme pressure agents, fatty materials, and corrosion inhibitors. Aqueous machining fluids used as lubricants and coolants in industrial processes are complex combinations of components which exhibit characteristics and functions peculiar to the process in which they are intended to be used. Aqueous machining fluids comprise water, lubricants and additives such as for example, extreme pressure agents, corrosion inhibitors, bactericides and fungicides. The lubricant component reduces friction between a tool and workpiece while the water helps dissipate the heat generated in the workpiece processing operation. Many different lubricants are used and aqueous machining fluids are further generally classified as soluble oils, synthetic and semi-synthetic fluids according to characteristics pertaining to the lubricants. Synthetics are characterized as being clear and containing lubricants other than oils. Semi-synthetics are characterized as being translucent or transparent and containing mineral oil. Soluble oil products are characterized as being opaque and comprising emulsions of petroleum based oils. The lubricants and many other components of the aqueous based machining liquids are synthetic or naturally occurring organic compounds or mixtures of such compounds. Lubricants used in the aqueous based machining liquids may include for example esters, amides, polyethers, amines and sulfonated oils. Corrosion inhibitors are employed to reduce or prevent corrosion of workpieces as well as to reduce or prevent chemical attack on the tool. Bactericides and fungicides are used to reduce or prevent microbial or fungal attack on the constituents of the liquid, while surfactants may be employed to form a stable suspension of water insoluble components in the water phase of the liquid. Thus each component has a function contributing to the overall utility and effectiveness of the machining liquid.

It will be appreciated that as a consequence of the complexity of machining fluids, fluids of the same type but having different compositions can have markedly different misting characteristics. It is thus highly desirable to provide a convenient method and apparatus for documenting the misting characteristics of machining fluids under conditions which closely approximate the intended conditions of use. Clearly, it is desirable to have methods and apparatus for evaluating effects of composition changes on misting properties of such fluids.

Figure 1:
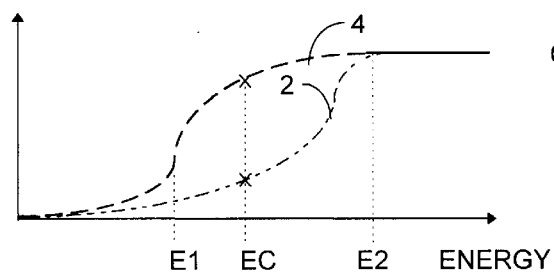
FIG. 1 is a diagram illustrating the relationship between energy and mist generation.

The method of the present invention contemplates use of a mist generating process for which energy input to a fluid can be controlled so that mist concentrations generated by fluids of different compositions under the same mist producing conditions can be compared to characterize the mist generating properties of the fluids. FIG.1 is a graph illustrating the relationship between mist concentration and energy input in a mist generating process at constant fluid volume. At energy levels below E1, mist generation is negligible. At energy levels above E2, mist generation is limited only by fluid volume. Useful comparative data of misting property of fluids is obtained at energy levels in the band between E1 and E2. In FIG. 1, curves 2 and 4 define an envelope of misting characteristics expected for fluids of different compositions, curve 4 illustrative of a fluid composition producing relatively greater concentrations of mist at relatively lower input energy levels as compared to that illustrated by curve 2. In accordance with the method of the invention, misting properties of fluids are characterized at a constant energy input level, for example EC in FIG. 1. That is, for comparison of misting properties, fluids of various compositions are subjected to an input energy in a mist generating means corresponding to a constant energy level and the resulting mist concentrations are recorded.

According to the method of the present invention, a sample of fluid of interest for measurement of a misting property is supplied to means for mist generation within an enclosure. Energy input to the fluid by the mist generating means is controllable, preferably adjustable to a nominal level such as EC of FIG. 1. Mist laden gas flows at a predetermined rate within the enclosure from the vicinity of the mist generating means to a sensor or instrument for measuring mist concentration. Relatively large droplets, hence droplets of relatively large mass are removed from the flow of mist laden gas before the gas reaches the sensor.

Mist generating apparatus in accordance with the invention shall be described with reference to FIG. 2, illustrative of a preferred embodiment. In FIG. 2, an enclosure 10 includes a reservoir 12 for fluid and mist generating means comprising a controlled rotating cylindrical member 16 on to which a controlled fluid stream is directed through nozzle 26. It will be appreciated other apparatus which is suitable for generating mist characterized by droplets of various masses and providing random droplet motion may be substituted for the combination of fluid stream and rotating cylindrical member 16. For example, atomizers could be used which are configured to provide aerosol streams in multiple directions and which are supplied with controllable gas and fluid flows. Alternatively, one or more disks rotatable at controllable speeds could be substituted for rotating cylindrical member 16, provided that a controllable supply of fluid to impact the disks were provided to insure generation of mist of the desired characteristics.

Within enclosure 10, mist generation occurs within a confined volume defined by the floor and sidewalls and a baffle 30 proximate the rotating member. An inlet 14 in enclosure 10 admits outside air proximate the mist generation means. Sensor 28 includes means 34, such as a diaphragm pump, to induce a flow of mist laden gas from the confined volume proximate rotating member 16, past baffles 30 and into inlet port 38 and through sensor 28 outside enclosure 10. Sensor 28 measures mist concentration. The confinement of the mist generating means effects removal of larger droplets from the mist laden gas facilitating measurement of concentrations of mist comprised predominantly by droplets of mass believed to dominate mists in areas of concern for human exposure in industrial environments.

Cylindrical member 16, preferably a grinding wheel, is rotatably supported within enclosure 10 and is rotated by spindle 18. Spindle 18 is driven by a motor 20, preferably a variable speed motor. Speed control 22 permits speed of rotation of cylindrical member 16 to be predeterminately varied by varying the speed of motor 20, the surface speed of member 16 having a significant affect on energy input to the fluid stream impacting member 16.

A recirculation pump 24 removes fluid from reservoir 12 at drain 36 and discharges a stream of fluid through nozzle 26 to contact rotating cylindrical member 16. The combined effect of drain 36, recirculation pump 24 and nozzle 26 is to recirculate fluid from reservoir 12 through a mist generator, hence simulating the recirculation of machining fluids typical in machining operations. Speed of recirculation pump 24 is preferably set according to the volume of reservoir 12 to enable complete recirculation of the fluid on a cycle of, for example, one recirculation of reservoir contents every one to two minutes.

In addition to control of rate of rotation of member 16, to affect energy input to the fluid by the mist generating means, it is preferable to provide means to vary the rate of flow of fluid from nozzle 26. In the preferred embodiment, flow rate is determined by speed of recirculation pump 24. Alternative means may be used to control the flow rate of fluid at nozzle 26, for example, a valve could be interposed between recirculation pump 24 and nozzle 26 permitting use of a constant speed recirculation pump; or, were the mist generating means to employ an atomizer rather than a rotating member, a pressure controlled accumulator could be supplied with fluid from reservoir 12 to supply fluid at a controlled pressure to a fluid inlet of the atomizer, the recirculation pump 24 then maintaining a supply of fluid to the pressure controlled accumulator. Irrespective of the configuration of the mist generating means, a gauge, for example pressure gauge 32 in the stream of fluid supplied to nozzle 26 is preferably inserted within the recirculation path to indicate visibly outside the enclosure that fluid is flowing.

As previously stated, generation of mists in machining operations produces droplets of various masses, the droplets of least mass being susceptible of transportation farthest from the source. To mimic the transportation of these droplets in an industrial process, enclosure 10 is constructed to generate a flow of gas from inlet 14 through sensor 28. Hence, with the exception of inlet 14 and inlet port 38 of sensor 28, enclosure 10 is sealed against infiltration of outside air. The induction of gas samples by means 34 into sensor 28, establishes, in combination with inlet 14, flow from the vicinity of mist generation through the path defined by baffles 30 to inlet port 38 of sensor 28. Larger, and hence heavier droplets, are separated from the gas by gravity and inertia, the droplets falling back into reservoir 12 or collecting on inside surfaces of enclosure 10 and on the surfaces of baffles 30 from which, under the influence of gravity, they fall or flow to recombine with fluid in reservoir 12. This separation of larger droplets simulates the effects of inertia and gravity on droplets of relatively large mass in machining operations.

Sensor 28 extracts samples of mist laden gas and measures the concentration of mist in the samples. Various instruments are known for measurement of mist concentration, for example: gravimetric type samplers such as electrostatic precipitators and glass fiber or polytetraflouroethane filters; cascade impactor type samplers; and, real time aerosol monitors. Applicants have chosen the DATA RAM™ aerosol monitor available from Monitoring Instruments for the Environment, Inc. of Billerica, MA, an instrument using light scattering for measurement of mass concentration of airborne particles. Means 34 within this instrument inducts gas at a selectable flow rate through inlet port 38, exhausting the gas through a filter (not shown) outside of enclosure 10. Sensor 28 performs measurements periodically, the repetition rate of measurements being adjustable. Sensor 28 preferably includes data storage for measurement data or other devices for recording measurement data, such as a numeric or alpha-numeric printer or recording plotter.

Figure 3:
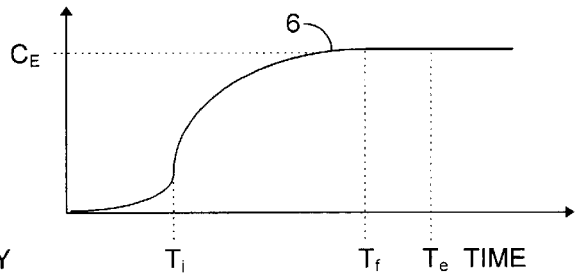
FIG. 3 is a diagram illustrating the relationship of time and mist concentration measurements in accordance with the preferred embodiment.

Applicants have found that for any fluid tested, mist concentration measurements produced by the apparatus of the preferred embodiment tend toward an equilibrium value $C_E$ over time. In FIG. 3, curve 6 illustrates the relationship of mist concentration values and time experienced with apparatus according to the preferred embodiment. Initially, the rate of change of values is low, up to an initial time value $T_i$. This period reflects the delay from commencement of a test of a fluid sample until significant quantities of droplets are transported to inlet port 38. Thereafter the rate of change of mist concentration measurement values increases until a time $T_f$ beyond which the measurement values do not change as a function of time. The period between $T_i$ and $T_f$ corresponds to the period required for substantial quantities of mist to accumulate within the confined volume proximate rotating member 16 and the attendant increased rate of transportation of droplets of small mass to inlet port 38. Beyond time $T_f$ an equilibrium is reached at which the rate of generation of mist, the rate of transportation of mist through sensor 28 and the rate of collection of droplets on the inside surfaces of enclosure 10 and baffles 30 are in balance, characteristic of the fluid under test at the predetermined energy input level EC. To eliminate the influence of changing values of mist concentration over time, applicants average the values of mist concentration measured during a period commencing at time $T_f$ and continuing for a predetermined interval to a time $T_e$. The average value thus produced for a fluid sample is used for comparison with like values obtained for other fluid samples.

For convenience, enclosure 10 is constructed in stackable sections, the lowermost section being open at the top for ease of access to rotatable member 16. When assembled, the seams formed where two sections are joined are sealed, insuring that substantially all gas admitted to enclosure 10 enters through inlet 14.

Calibration

Apparatus according to the invention is calibrated by comparison of measurements of mist concentration produced by the apparatus with measurements made for the same fluid(s) in a production environment. In this regard, it will be appreciated that sensor 28 should be the same as the sensor used to make measurements in the production environment, and adjusted to induce the same rate of flow of gas through the sensor as used in making measurements in a production environment. Mist concentration measurements are made for a fluid of interest proximate equipment executing a machining process. Fresh fluid is used to eliminate effects of fluid contamination on the mist concentrations produced by the fluid. Should it be desired to use the apparatus to characterize misting properties of fluids of different types, measurements for exemplary fluids of each type are made in the production environment. Distance of the sensor from the source of mist is preferably selected to approximate the intended location of an equipment operator relative to the dominate mist source of the equipment, but in any case, a location is chosen to avoid splashing of the sensor with fluid ejected from the machining process while permitting measurement of mist concentrations within the extremes of the measurement range of the sensor. If required, process parameters, such as fluid flow rate, and rates of rotation of rotating members can be adjusted to insure the measurements of mist concentration are not at the extremes of the measurement range. Plural measurements are taken to permit statistical elimination of aberrations attributable to phenomena in the production environment such as air currents caused by activities proximate but unrelated to the machining process. The process of measurement in a production environment is repeated for samples of fluids of different types or fluids of the same type taken from different production batches and the data recorded, precautions being taken to use fresh fluid for each sample used for data collection.

Using the data gathered from the production environment, a sample of the same fluid is placed in reservoir 12. With the flow of gas through sensor 28 selected to the same rate employed in connection with measurements made in the production environment, the rate of rotation of cylindrical member 16 and the rate of flow of fluid through nozzle 26 are adjusted to produce mist concentration measurements nearly equal to those recorded in the production environment for the same fluid. As with the production environment data collection, plural measurements are made and recorded to permit statistical elimination of aberrations. In particular, mist concentration measurements are made by operation of the apparatus for approximately sixty (60) minutes for each fluid sample, the average value of mist concentration measurements made during the last fifteen (15) minutes of operation being used to adjust the rates of rotation and pump speed. The rates of rotation and pump speed are recorded.

After collection of data with the first fluid sample, the fluid is removed, the inside surfaces of the reservoir and enclosure cleaned, sensor 28 purged, and a sample of a fluid of different composition or fluid of different type is placed in reservoir 12. Measurements are made and recorded without altering the flow rate or rate of rotation of cylindrical member 16. As with the first fluid, mist concentration measurements are made for approximately sixty (60) minutes, and the average of measurement values produced during the last fifteen (15) minutes is used in the calibration procedure. These data are compared with data obtained from the production environment for the same fluid. If mist concentration values are within 5%, calibration is complete, and the fluid sample is removed and the entire apparatus is cleaned as before in preparation for use in data collection.

If the mist concentration values produced for the second fluid sample deviate from the values obtained in the production environment by more than 5%, the rate of rotation of cylindrical member 16, and/or the rate of flow of fluid through nozzle 26, are adjusted to reduce the deviation to within 5%. Rates of rotation and pump speed are recorded, the fluid sample is removed and the apparatus is cleaned. A fresh sample of the first fluid is then placed in reservoir 12 and with the same rate of rotation of cylindrical member 16 and pump speed established for the second fluid sample, mist concentration measurements are made. If the deviation of these values of mist concentration measurements are within 5% of the values obtained for the same fluid in the production environment, no further adjustment of rate of rotation of cylindrical member 16 or fluid flow rate is required and calibration is complete. If not, the calibration process is repeated using samples of fluids of two different compositions a combination of rate of rotation of cylindrical member 16 and fluid flow rate is found so that measurement data for both fluid compositions produced by the apparatus is within 5% of the corresponding data recorded in the production environment.

Data recorded from calibration of an apparatus constructed in accordance with the invention were as follows:

TABLE 1

| Fluid Type | Mist Concentration mg/cm³ (Production Environment) | Mist Concentration mg/cm³ (Apparatus) |
|---|---|---|
| Synthetic | 1.6 | 1.6 |
| Soluble Oil | 2.5 | 2.5 |
| Semi-synthetic* | 5.0 | 4.9 |

*The semi-synthetic was not used in the calibration procedure, but mist concentration measurements were made in the production environment and with the apparatus calibrated in accordance with the calibration procedure for purposes of comparison.

EXAMPLES

Following calibration, applicants used the apparatus of the invention to collect data on various fluid samples as set forth in the following Examples. Prior to commencement of data collection for a sample, the inside surfaces of the enclosure were cleaned and dried, and sensor 28 was purged. A sample of a fluid for an example was placed in reservoir 12, the seams of the enclosure were sealed, sensor 28 was activated, and pump 24 and motor 20 were started, pump speed and motor speed being the same as established through calibration. For each fluid sample, the apparatus was operated for approximately sixty (60) minutes. The recorded values of mist concentration are the average of measurements made by sensor 28 during the last fifteen (15) minutes of operation for each fluid sample. This period of data collection corresponds to the period from time $T_e$ to time $T_f$ of FIG. 3. For purposes of comparison of fluid misting properties of fluids, only the average values of mist concentration are considered. In this way, misting properties of fluids are characterized using data for which aberrations of measurements are statistically eliminated. Following completion of data collection for a fluid sample, enclosure 10 of the apparatus was dismantled, the inside surfaces, including surfaces of baffles 30, were cleaned and dried, sensor 28 was purged, and the fluid recirculation path, including recirculation pump 24, nozzle 26, guage 32 and associated connecting conduits, is purged to prepare the apparatus for the next fluid sample.

The following data were obtained following the aforesaid procedure with according to the invention using samples of fluids as indicated:

TABLE 2

| Example No. | Fluid Type | Oil Content (Weight %) | Mist Concentration (mg/cm³) |
|---|---|---|---|
| 1 | Water | 0 | 1.00 |
| 2 | Synthetic 1 | 0 | 1.64 |
| 3 | Synthetic 2 | 0 | 1.35 |
| 4 | Synthetic 3 | 0 | 1.72 |
| 5 | Synthetic 4 | 0 | 1.60 |
| 6 | Semi-synthetic 1 | 6.5 | 1.65 |
| 7 | Semi-synthetic 2 | 15.0 | 1.51 |
| 8 | Semi-synthetic 3 | 25.0 | 1.78 |
| 9 | Semi-synthetic 4 | 26 | 3.0 |
| 10 | Soluble Oil 1 | 19.2 | 1.89 |
| 11 | Soluble Oil 2 | 62 | 2.56 |
| 12 | Soluble Oil 3 | 49 | 2.58 |
| 13 | Soluble Oil 4 | 52 | 2.29 |
| 14 | Soluble Oil 5 | 60 | 3.5 |
| 15 | Soluble Oil 6 | 79 | 2.80 |
| 16 | Soluble Oil 7 | 85 | 4.11 |

While the preferred embodiments have been described in detail herein with reference to the accompanying drawings, it is not intended that the scope of the invention be limited to the preferred embodiment or such details. Rather, it is intended that the scope of the invention be considered to include all modifications, alterations, and equivalents falling within the spirit and scope of the appended claims.

What is claimed is:

1. Method for characterizing a misting property of fluids comprising the steps of:

a) generating mist from a fluid, the mist being generated within an enclosure;

b) controlling the level of energy input to the fluid to generate the mist;

c) producing a flow of gas at a predetermined flow rate from the vicinity of generation of the mist through a predetermined distance within the enclosure to a device for measuring mist concentration, whereby gas transport of a mist laden gas occurs within the enclosure, the mist laden gas being admitted to the device through an inlet port;

d) removing droplets of relatively large mass from the mist laden gas before the mist laden gas reaches the inlet port;

e) repeating the preceding steps with samples of plural fluids of different compositions, for each fluid sample the level of energy input to the fluid being substantially the same; and f) comparing the values of mist concentration produced from the plural fluids whereby a misting property of the fluids is characterized.

2. The method of claim 1 wherein the step of generating mist further comprises contacting a stream of the fluid with a rotating member.

3. The method of claim 1 wherein the step of producing a flow of gas further comprises admitting air to the enclosure in the vicinity of generation of the mist and exhausting mist laden gas from the enclosure at the mist concentration measuring device.

4. The method of claim 1 further comprising the step of recirculating the fluid from a reservoir through means for generating mist.

5. The method of claim 1 wherein the fluid is a metalworking fluid.

6. The method of claim 1 further comprising the step of recording plural measurements of mist concentration for each fluid sample.

7. The method of claim 2 wherein the rotating member is an abrasive wheel.

8. The method of claim 2 wherein the step of controlling the level of energy input to the fluid comprises controlling a rate of rotation of the rotating member.

9. The method of claim 2 wherein the step of controlling the level of energy input to the fluid comprises controlling a rate of flow of the fluid stream contacting the rotating member.

10. The method of claim 2 wherein the step of controlling the level of energy input to the fluid comprises controlling a rate of flow of the fluid stream contacting the rotating member and controlling a rate of rotation of the rotating member.

11. The method of claim 5 wherein the metalworking fluid is an aqueous metalworking fluid.

12. An apparatus for characterizing a misting property of fluids, the misting property characterized by comparing mist concentration levels produced by plural fluid samples, the apparatus comprising:

a) a mist generating means within an enclosure;

b) means for controlling the level of energy input by the mist generating means to a fluid supplied to the mist generating means;

c) means for producing a flow of gas at a predetermined flow rate from the vicinity of the mist generating means through a predetermined distance within the enclosure, whereby gas transport of a mist laden gas occurs within the enclosure;

d) a device for measuring mist concentration, the device having an inlet port for admitting the mist laden gas;

e) means for removing droplets of relatively large mass from the mist laden gas before the mist laden gas reaches the inlet port; and f) means for recording measurements of mist concentration to permit comparison of mist concentrations produced from samples of plural fluids.

13. The apparatus of claim 12 wherein the means for generating mist from the fluid further comprises a rotating member and means for contacting a stream of the fluid with the rotating member.

14. The apparatus of claim 12 wherein the means for removing droplets of relatively large mass produce changes of direction of the flow of gas between the mist generating means and the inlet port.

15. The apparatus of claim 12 further comprising a reservoir for containing a fluid and means for recirculating fluid from the reservoir through the mist generating means.

16. The apparatus of claim 13 wherein the means for controlling energy input to the fluid further comprises means for predeterminately varying a rate of rotation of the rotating member.

17. The apparatus of claim 13 wherein the means for controlling energy input to the fluid further comprises means for adjusting a rate of flow of the fluid stream contacting the rotating member.

18. The apparatus of claim 13 wherein the means for controlling energy input to the fluid further comprises means for adjusting a rate of flow of the fluid stream contacting the rotating member and means for predeterminately varying a rate of rotation of the rotating member.

* * * * *